(12) United States Patent
Goshgarian

(10) Patent No.: US 7,105,015 B2
(45) Date of Patent: Sep. 12, 2006

(54) METHOD AND SYSTEM FOR TREATING AN OSTIUM OF A SIDE-BRANCH VESSEL

(75) Inventor: Justin Goshgarian, Santa Rosa, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 75 days.

(21) Appl. No.: 10/464,716

(22) Filed: Jun. 17, 2003

(65) Prior Publication Data

US 2004/0260378 A1 Dec. 23, 2004

(51) Int. Cl.
*A61F 2/06* (2006.01)

(52) U.S. Cl. .................. 623/1.11; 604/101.05

(58) Field of Classification Search ........ 623/1.1–1.15, 623/1.23, 1.35; 604/101.01–101.5
See application file for complete search history.

(56) References Cited

U.S. PATENT DOCUMENTS

| | | | |
|---|---|---|---|
| 4,140,126 A * | 2/1979 | Choudhury | ............... 606/194 |
| 4,739,762 A | 4/1988 | Palmaz | |
| 5,133,732 A | 7/1992 | Wiktor | |
| 5,292,331 A | 3/1994 | Boneau | |
| 5,421,955 A | 6/1995 | Lau et al. | |
| 5,607,444 A | 3/1997 | Lam | |
| 5,632,762 A | 5/1997 | Myler | |
| 5,749,890 A * | 5/1998 | Shaknovich | ............... 606/198 |
| 5,755,771 A | 5/1998 | Penn et al. | |
| 5,906,640 A | 5/1999 | Penn et al. | |
| 6,013,085 A | 1/2000 | Howard | |
| 6,027,526 A | 2/2000 | Limon et al. | |
| 6,090,127 A | 7/2000 | Globerman | |
| 6,183,503 B1 * | 2/2001 | Hart et al. | ................... 623/1.1 |
| 6,258,073 B1 | 7/2001 | Mauch | |
| 6,361,544 B1 | 3/2002 | Wilson et al. | |
| 6,527,739 B1 | 3/2003 | Bigus et al. | |
| 2002/0099406 A1 | 7/2002 | St. Germain | |

FOREIGN PATENT DOCUMENTS

| | | |
|---|---|---|
| WO | WO 1998/47446 | 10/1998 |
| WO | WO 2001/34061 | 5/2001 |
| WO | WO 2002/056799 | 7/2002 |

* cited by examiner

*Primary Examiner*—Bruce Snow

(57) ABSTRACT

The present invention provides a method and system for treating an ostium of a side-branch vessel. The system includes a catheter, a first inflatable member, a stent disposed on the first inflatable member, and a second inflatable member. The first inflatable member is disposed on a distal portion of the catheter, while the second inflatable member is disposed on a proximal portion of the catheter. The first inflatable member is inflated a first time to expand the stent within the side branch. The first inflatable member is then deflated, advanced, and inflated a second time to anchor the system while the second inflatable member is inflated to conform a portion of the stent to the ostium of the side-branch vessel.

16 Claims, 7 Drawing Sheets

METHOD AND SYSTEM FOR TREATING AN OSTIUM OF A SIDE-BRANCH VESSEL

TECHNICAL FIELD

This invention relates generally to biomedical devices that are used for treating vascular conditions. More specifically, the invention relates to a method and system for treating an ostium of a side-branch vessel.

BACKGROUND OF THE INVENTION

Heart disease, specifically coronary artery disease, is a major cause of death, disability, and healthcare expense in the United States and other industrialized countries. A number of methods and devices for treating coronary heart disease have been developed, some of which are specifically designed to treat the complications resulting from atherosclerosis and other forms of coronary arterial narrowing.

One method for treating such conditions is percutaneous transluminal coronary angioplasty (PTCA). During PTCA, a balloon catheter device is inflated to dilate a stenotic blood vessel. The stenosis may be the result of a lesion such as a plaque or thrombus. When inflated, the pressurized balloon exerts a compressive force on the lesion, thereby increasing the inner diameter of the affected vessel. The increased interior vessel diameter facilitates improved blood flow. Soon after the procedure, however, a significant proportion of treated vessels restenose.

To prevent restenosis, stents, constructed of a metal or polymer and generally cylindrical in shape and hollow, are implanted within the vessel to maintain lumen size. The stent acts as a scaffold to support the lumen in an open position. Configurations of stents include a cylindrical sleeve defined by a mesh, interconnected stents, or like segments. Exemplary stents are disclosed in U.S. Pat. No. 5,292,331 to Boneau, U.S. Pat. No. 6,090,127 to Globerman, U.S. Pat. No. 5,133,732 to Wiktor, U.S. Pat. No. 4,739,762 to Palmaz and U.S. Pat. No. 5,421,955 to Lau.

Stent insertion may cause undesirable reactions such as inflammation, infection, thrombosis, and proliferation of cell growth that occludes the passageway. To assist in preventing these conditions, stents have been used with coatings to deliver drugs or other therapeutic agents at the site of the stent.

The efficacy of a stent may be reduced when repairing a vessel affected by stenosis at the point at which the vessel originates, branching off from an adjoining vessel. This point of origin is referred to as the ostium of the vessel. A lesion located at this point is termed an ostial lesion.

To repair an ostial lesion, a stent must cover the entire affected area without occluding blood flow in the adjoining vessel. However, when a conventional stent overlies the entire ostium of the affected vessel, it may also extend into the adjoining vessel, occluding blood flow to some degree. Furthermore, when the stent extends into the adjoining vessel, the stent may block access to portions of the adjoining vessel that require further intervention.

U.S. Pat. No. 5,749,890 to Shaknovich discloses a method and system for stent placement in an ostial lesion that ensures the stent does not extend into the adjoining vessel. However, the method and system do not ensure coverage of the affected area where it extends into the junction with the adjoining vessel. U.S. Pat. No. 5,607,444 to Lam describes an ostial stent having a flaring portion that provides coverage of at least a portion of a lesion at the junction of the two vessels. This invention, however, describes no means for actively conforming the stent to the shape of the specific ostium being treated.

Therefore, it would be desirable to have a method and system for treating an ostium of a side-branch vessel that overcomes the aforementioned and other disadvantages.

SUMMARY OF THE INVENTION

One aspect of the present invention is a system for treating an ostium of a side-branch vessel, comprising a catheter, a first inflatable member, a stent disposed on the first inflatable member, and a second inflatable member. The first inflatable member is disposed on a distal portion of the catheter; the second inflatable member is disposed on a proximal portion of the catheter. The first inflatable member is inflated a first time to expand the stent within the side branch. The first inflatable member is then deflated, advanced, and inflated a second time to anchor the system while the second inflatable member is inflated to conform a portion of the stent to the ostium of the side-branch vessel.

Another aspect of the present invention is a method for treating an ostium of a side-branch vessel. A catheter is inserted into a side-branch vessel, the catheter comprising a first inflatable member disposed on a distal portion of the catheter, a first stent disposed on the first inflatable member, and a second inflatable member disposed on a proximal portion of the catheter. The catheter is positioned such that the first stent is at least partially within the side-branch vessel and adjacent the ostium of the vessel. The first inflatable member is inflated to expand the first stent. The first inflatable member is deflated. The catheter is advanced to a position such that the second inflatable member is at least partially within the expanded stent and adjacent the ostium of the vessel. The first inflatable member is re-inflated to anchor the catheter within the side-branch vessel. The second inflatable member is inflated to conform a portion of the stent to the ostium of the side-branch vessel. The first and second inflatable members are deflated, and the catheter is removed from the side-branch vessel.

The aforementioned and other features and advantages of the invention will become further apparent from the following detailed description of the presently preferred embodiments, read in conjunction with the accompanying drawings. The detailed description and drawings are merely illustrative of the invention rather than limiting, the scope of the invention being defined by the appended claims and equivalents thereof.

DETAILED DESCRIPTION OF THE PRESENTLY PREFERRED EMBODIMENTS

Figure 1:
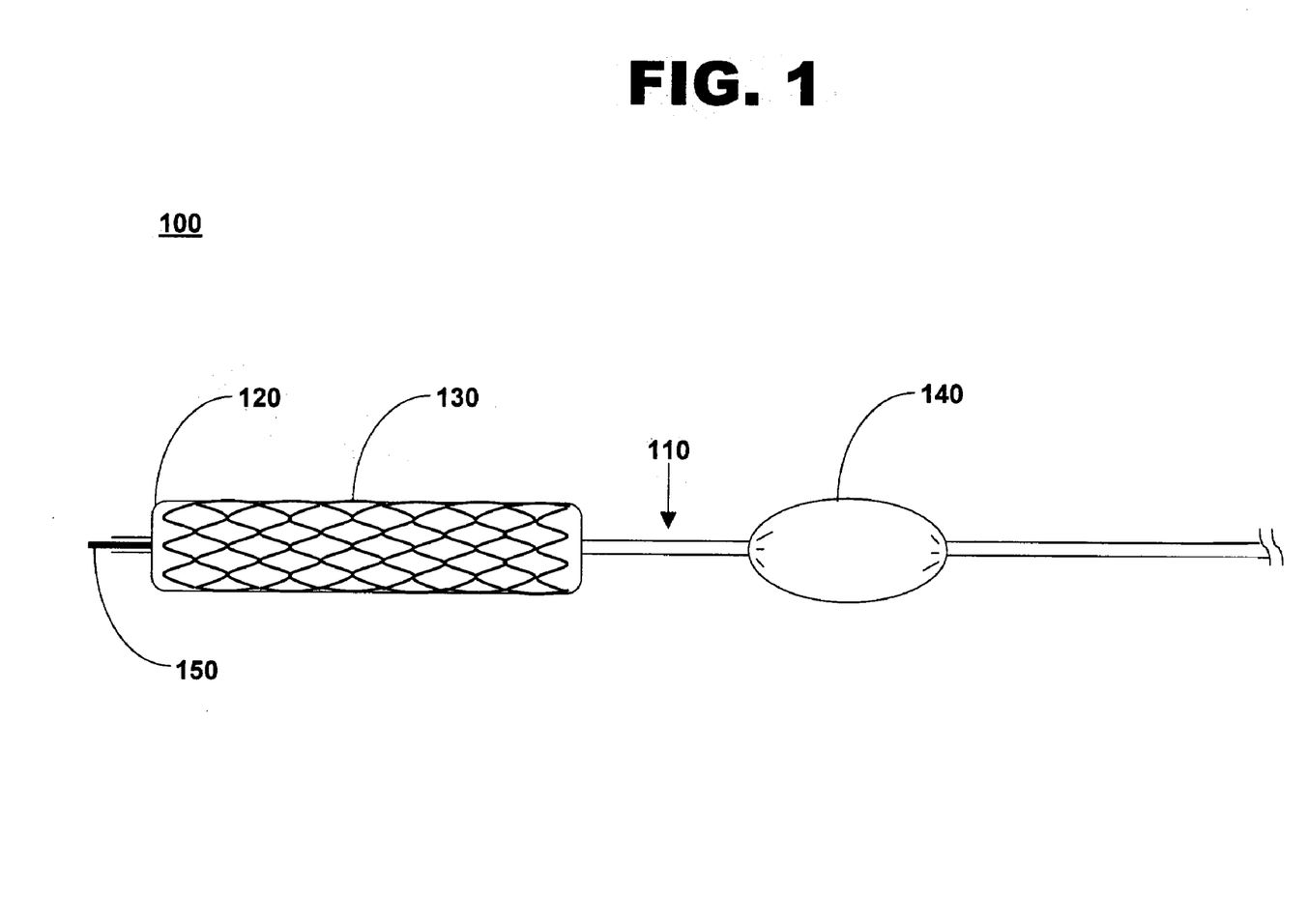
FIG. 1 is an illustration of one embodiment of a system for treating an ostium of a side-branch vessel, in accordance with the present invention.

One aspect of the present invention is a system for treating an ostium of a side-branch vessel. One embodiment of the system, in accordance with the present invention, is illustrated in FIG. 1 at 100. System 100 comprises a catheter 110, a first inflatable member 120, a stent disposed on the first inflatable member 130, a second inflatable member 140, and a guide wire 150. The system may further comprise at least one radiopaque marker (not shown) to aid in positioning the system. The stent may include a therapeutic agent (also not shown).

Catheter 110 may be any suitable catheter capable of inflating one or more inflatable members. Catheter 110 may be, for example, a low profile design with a tapered distal tip and an inner lumen for insertion of a conventional guide wire. Catheter 110 may include at least one hollow tubular portion that is in communication with inflatable members 120 and 140 in such a manner that inflatable members 120 and 140 may access a source of inflation. Because catheter 110 comprises consecutively placed inflatable members, system 100 may be used over a single guide wire 150, thereby reducing the number of elements introduced to the target treatment site.

First inflatable member 120 is disposed on a distal portion of the catheter. Member 120 may be, for example, an inflatable balloon of suitable compliance for expanding stent 130. Member 120 may be formed from a material such as polyethylene, polyethylene terephthalate (PET), or from nylon or the like. The length and diameter of the inflatable member may be selected to accommodate the configuration of stent 130. Member 120 is in communication with catheter 110 in such a manner that a source of inflation (such as a fluid source) may be delivered to the member via catheter 110.

First inflatable member 120 is inflated a first time to expand stent 130 within the side-branch vessel. Member 120 may become generally cylindrical upon inflation, providing a roughly uniform expansion of the stent.

Stent 130 may be made from a variety of medical implantable materials, including, but not limited to, stainless steel, nitinol, tantalum, ceramic, nickel, titanium, aluminum, polymeric materials, MP35N, stainless steel, titanium ASTM F63-83 Grade 1, niobium, high carat gold K 19–22, combinations of the above, and the like. Stent 130 may include a therapeutic agent such as an antineoplastic agent, an antiproliferative agent, an antibiotic, an antithrombogenic agent, an anticoagulant, an antiplatelet agent, an anti-inflammatory agent, combinations of the above, and the like.

After delivering stent 130, first inflatable member 120 is deflated. Member 120 may include a contractile member to aid in returning the inflatable member to an uninflated configuration upon deflation. The contractile member may be, for example, a band of elastic or shape-memory material that encloses at least a portion of the inflatable member. The contractile member may be affixed to the inflatable member, or the two members may be manufactured as an essentially unitary structure. The contractile member expands when the inflatable member is inflated and then contracts to draw the inflatable member back down to a compact profile that allows the system to be advanced to a position deeper within the side-branch vessel.

After being deflated and advanced within the vessel, first inflatable member 120 is inflated a second time to anchor system 100 while second inflatable member 140 is inflated to conform a portion of the stent to the ostium of the side-branch vessel.

Second inflatable member 140 is disposed on a proximal portion of the catheter. Second inflatable member 140 may be, for example, an inflatable balloon of suitable compliance for conforming a portion of stent 130 to the ostium of a side-branch vessel. Second inflatable member 140 may be formed from a material such as polyethylene, polyethylene terephthalate (PET), or from nylon or the like. It may comprise a material that is the same as or different from that comprising first inflatable member 120.

Second inflatable member 140 is in communication with catheter 110 in such a manner that a source of inflation may be delivered to member 140 via catheter 110. Member 140 may become generally spherical upon inflation. Inflation of member 140 causes the portion of stent 130 that is positioned nearest the ostium to further expand and conform to the shape of the ostium, assuming, for example, a flared configuration that mimics the shape of the ostium. This enables the stent to cover an entire affected area at the ostium of a side-branch vessel without protruding into the adjoining vessel and occluding blood flow in that vessel.

To aid in conforming stent 130 to the shape of the ostium, stent 130 may comprise a body portion and an end portion, these portions having different material properties or different geometric configurations. For example, the end portion may be made of a different, more malleable material than the body portion; or the end portion may have a geometric configuration that is more easily deformed than that of the body portion.

Figure 2:
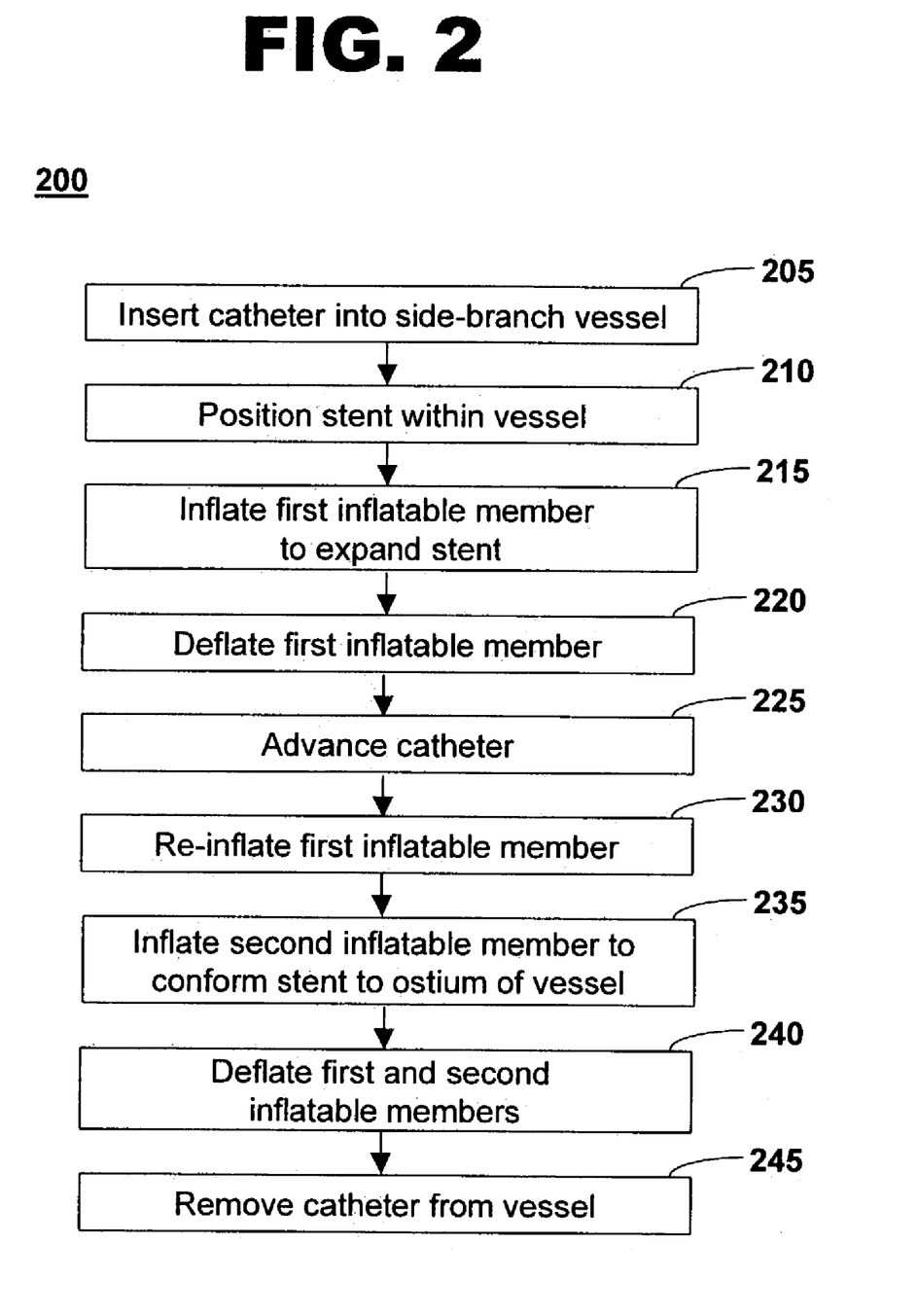
FIG. 2 is a flow diagram of one embodiment of a method for treating an ostium of a side-branch vessel, in accordance with the present invention.

Another aspect of the present invention is a method for treating an ostium of a side-branch vessel. FIG. 2 at 200 shows a flow diagram of one embodiment of a method in accordance with the present invention.

A catheter is inserted into a side-branch vessel (Block 205). The catheter comprises a first inflatable member disposed on a distal portion of the catheter, a first stent disposed on the first inflatable member, and a second inflatable member disposed on a proximal portion of the catheter. The catheter may further comprise at least one radiopaque marker to aid in positioning the catheter relative to the side-branch vessel. Because the catheter comprises consecutively placed inflatable members, as shown in FIG. 1, it may be used over a single guide wire, thereby reducing the number of elements introduced to the target treatment site.

The catheter is positioned such that the stent is at least partially within the side-branch vessel and adjacent the ostium of the vessel (Block 210). A portion of the stent may extend into the adjoining vessel.

The first inflatable member is inflated to expand the stent within the side-branch vessel (Block 215). The first inflatable member may become generally cylindrical upon inflation, providing a roughly uniform expansion of the stent. Where the stent includes a therapeutic agent, expanding the stent places the therapeutic agent in contact with the vessel wall.

The first inflatable member is deflated (Block 220), and the catheter is advanced to a position such that the second inflatable member is at least partially within the expanded stent and adjacent the ostium of the vessel (Block 225). The first inflatable member is then inflated a second time to anchor the catheter within the side-branch vessel (Block 230).

With the catheter anchored in the vessel by the first inflatable member, the second inflatable member is inflated (Block 235). The second inflatable member may become generally spherical upon inflation. Inflation of the second inflatable member conforms the portion of the stent that is nearest the ostium to the shape of the ostium. This portion may assume, for example, a flared configuration that mimics the shape of the ostium. This enables the stent to cover an entire affected area at the ostium of a side-branch vessel without protruding into the adjoining vessel and occluding blood flow in that vessel.

To aid in conforming the stent to the shape of the ostium, the stent may comprise a body portion and an end portion, these portions having different material properties or different geometric configurations. For example, the end portion may be made of a different, more malleable material than the body portion; or the end portion may have a geometric configuration that is more easily deformed than that of the body portion.

After the stent has been conformed to the ostium of the vessel, the first and second inflatable members are deflated (Block 240), and the catheter is removed from the side-branch vessel (Block 245).

FIGS. 3a–3d illustrate various steps of the method described in FIG. 2, showing the positions of a catheter 310, a first inflatable member 320, a stent 330, and a second inflatable member 340 in relation to a side-branch vessel 350 and an adjoining vessel 360.

Figure 3A:
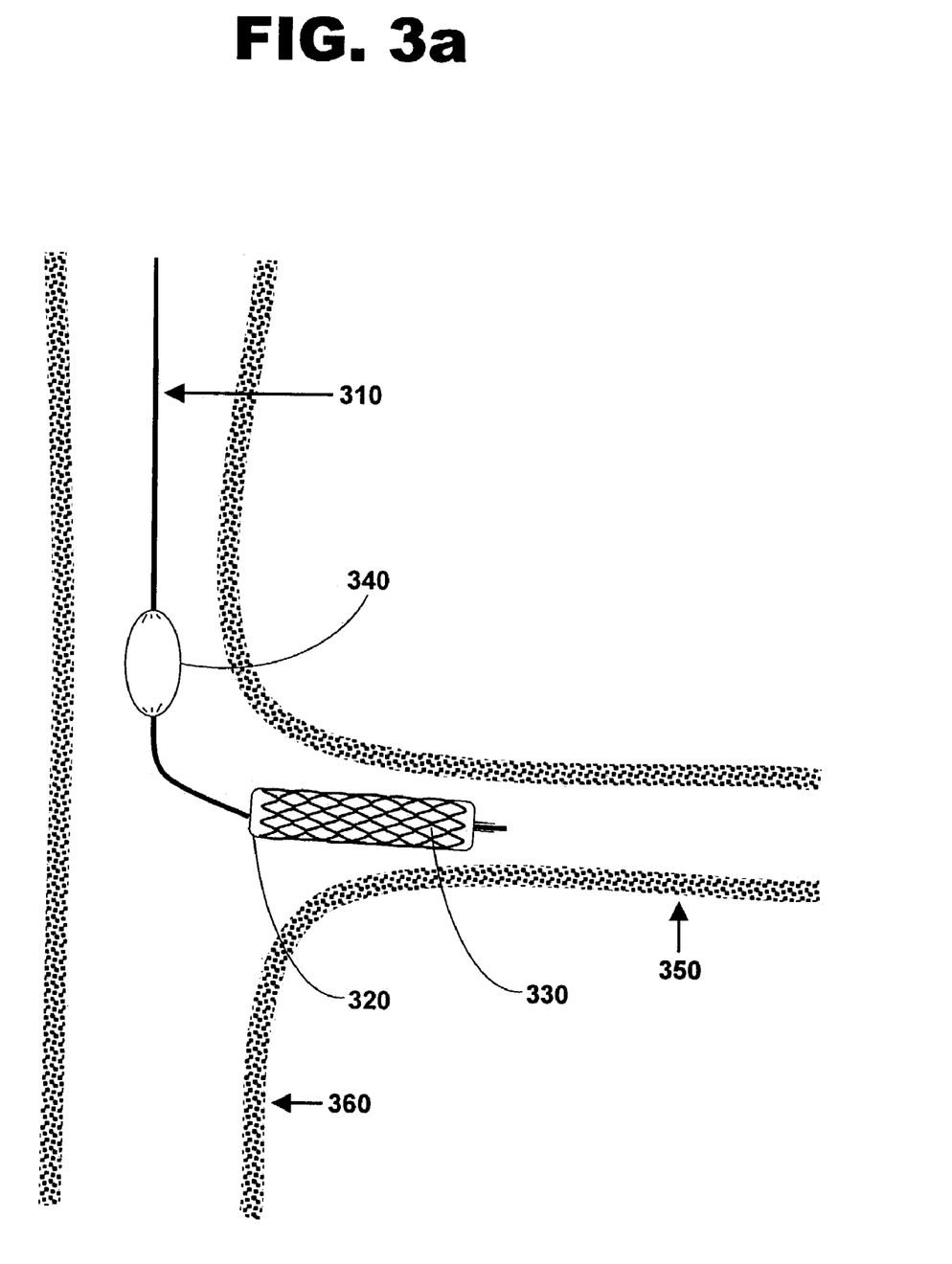
FIGS. 3*a*–3*d* illustrate the method described in FIG. 2.
Figure 3B:
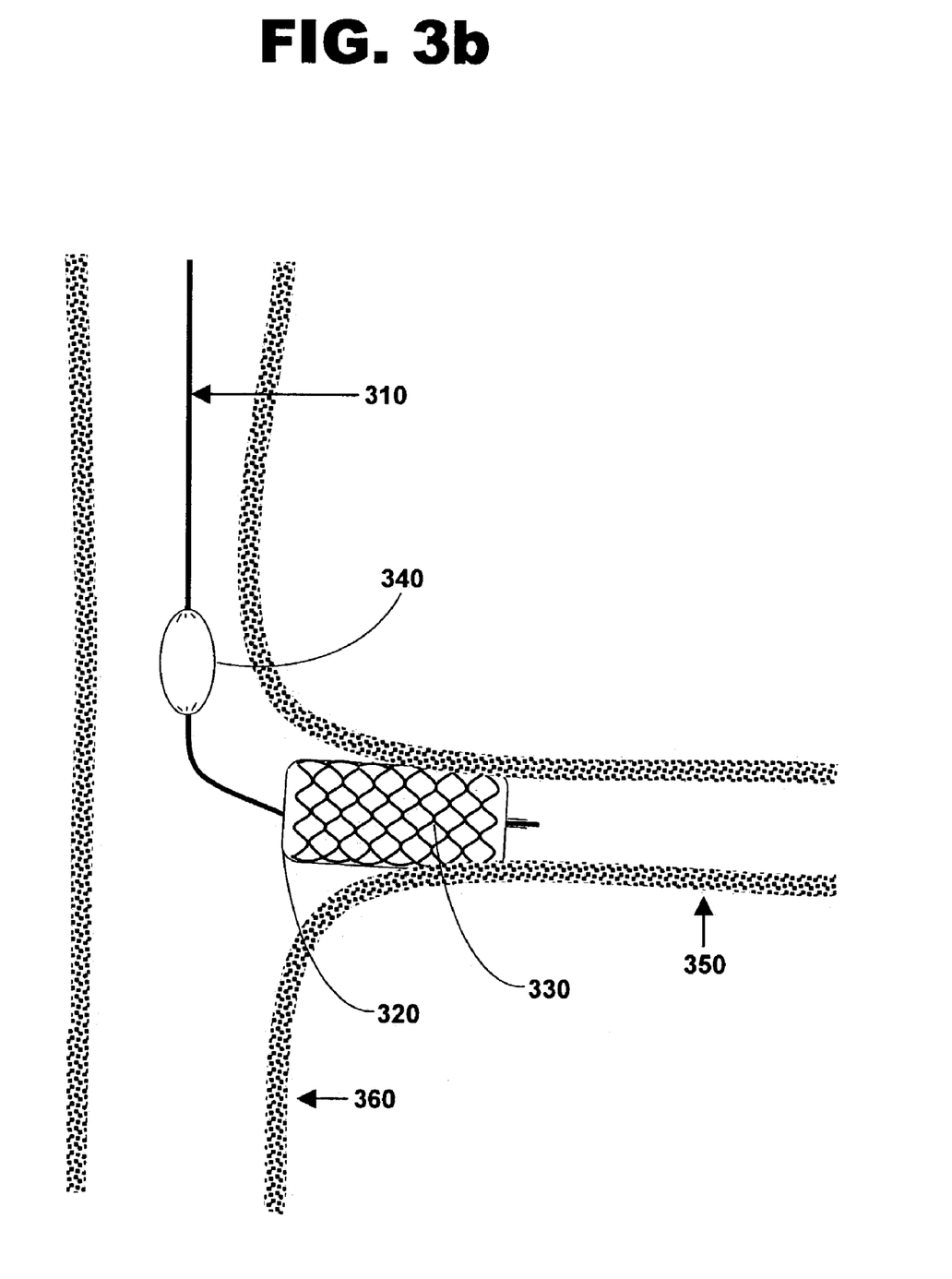
Figure 3C:
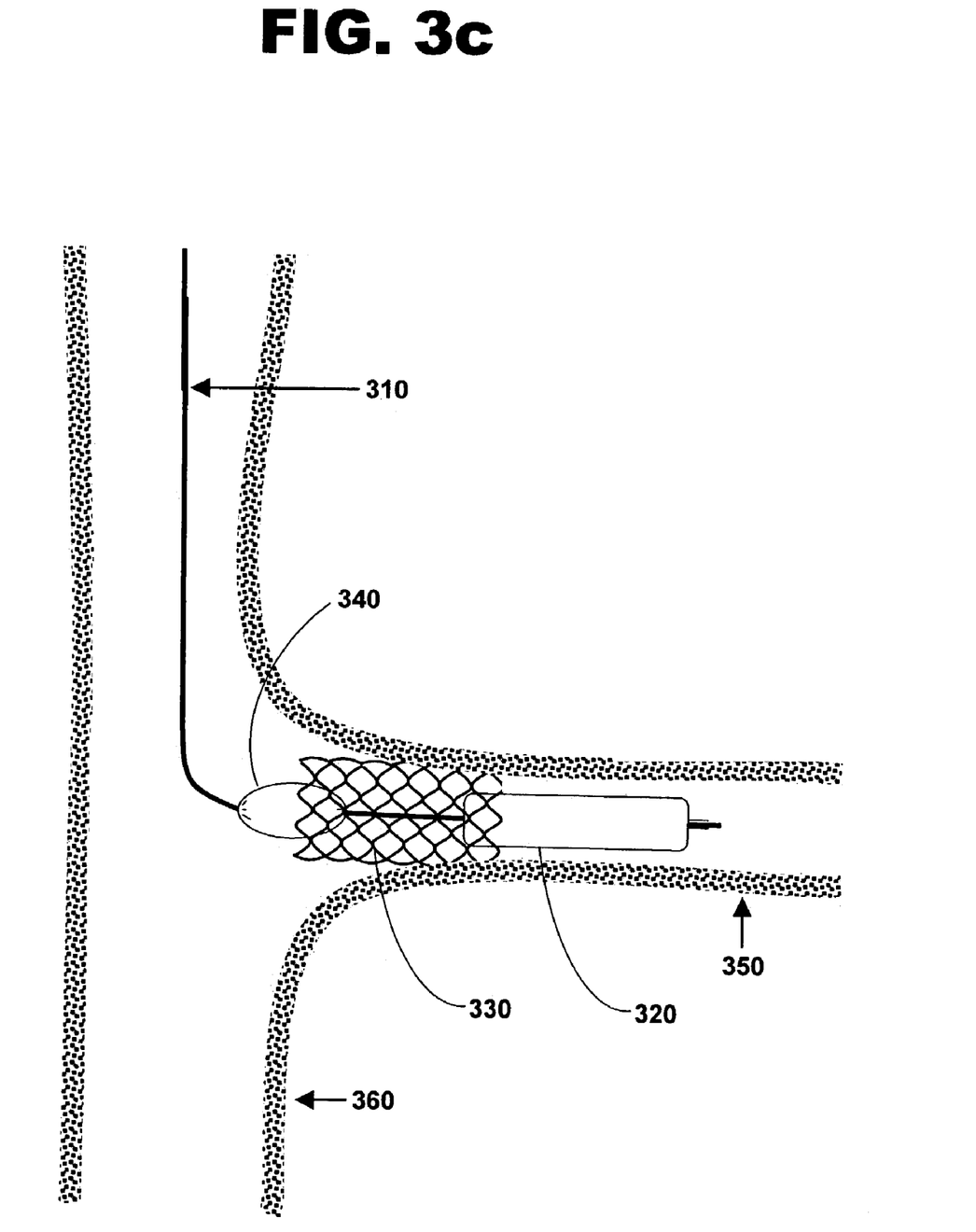
Figure 3D:
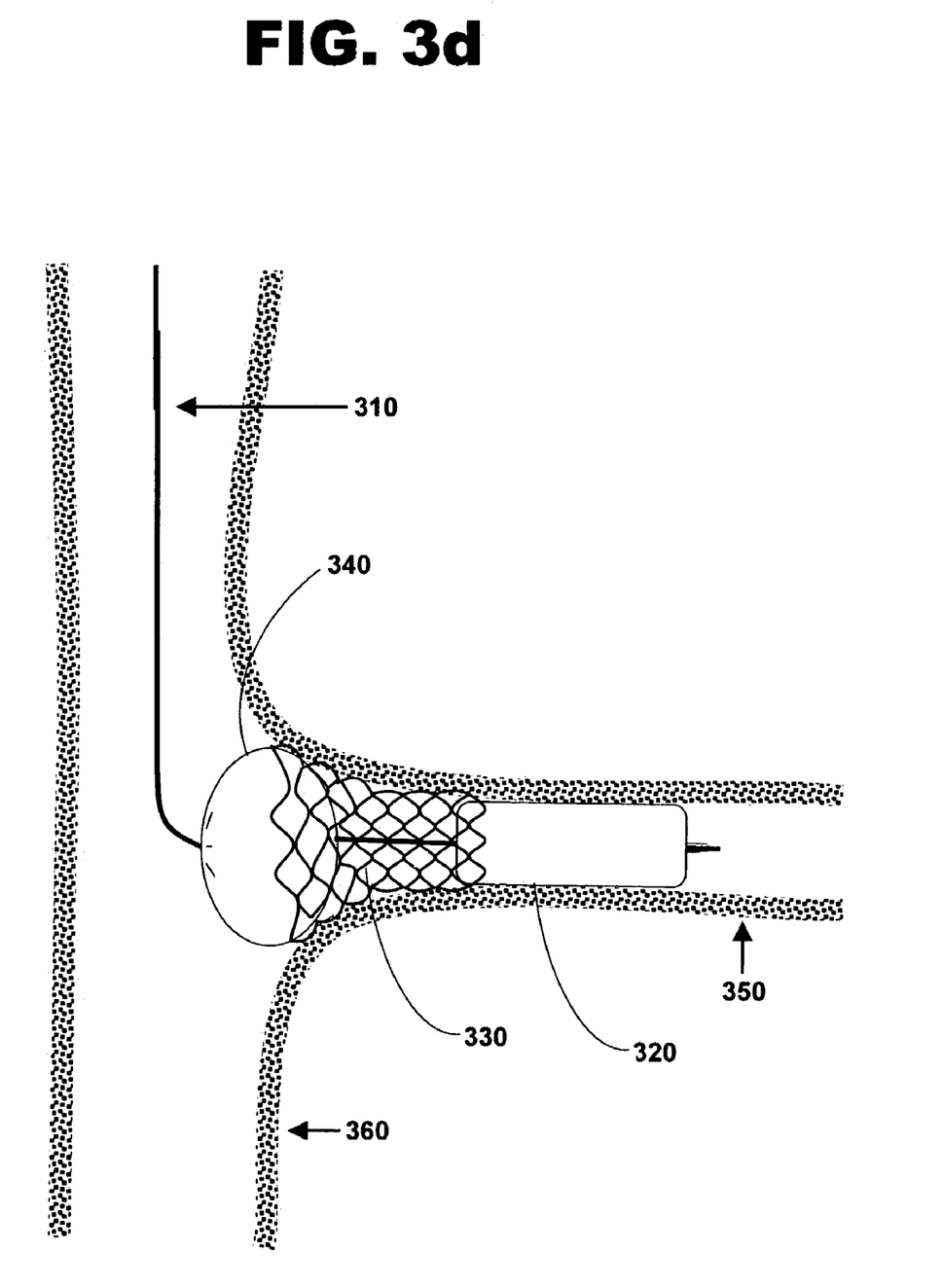

FIG. 3a shows catheter 310 positioned such that unexpanded stent 330 is partially within side-branch vessel 350 and adjacent the ostium of the vessel. In FIG. 3b, first inflatable member 320 has been inflated, expanding stent 330. FIG. 3c shows first inflatable member 320 deflated and advanced deeper into side-branch vessel 350 such that second inflatable member 340 is partially within expanded stent 330 and adjacent the ostium of the vessel. In FIG. 3d, first inflatable member 320 has been inflated to anchor the catheter in side-branch vessel 350. Second inflatable member 340 is also shown inflated, conforming stent 330 to the ostium of the vessel.

Figure 4:
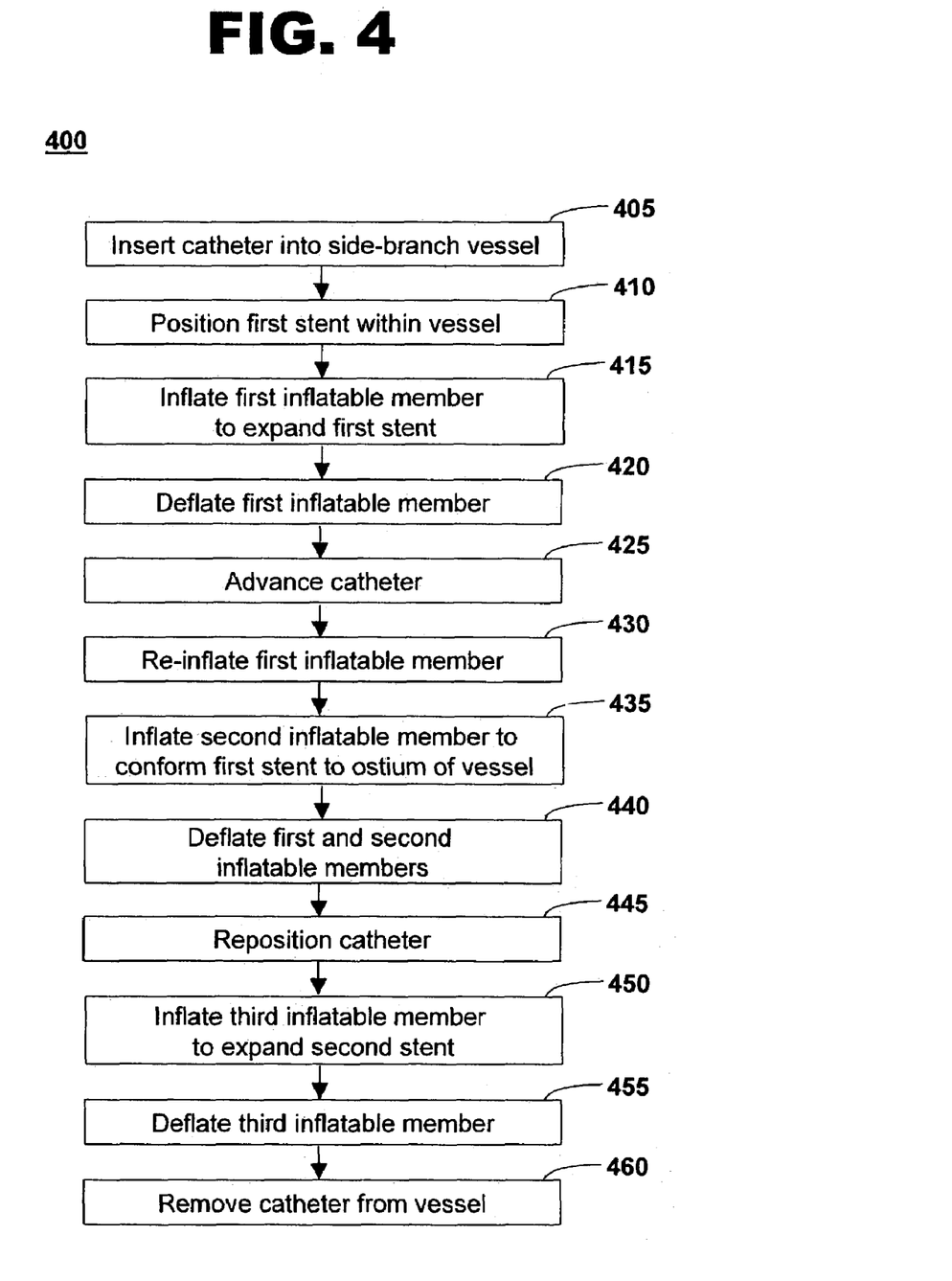
FIG. 4 is a flow diagram of another embodiment of a method for treating an ostium of a side-branch vessel, in accordance with the present invention.

A further aspect of the present invention is a method for treating an ostium of a side-branch vessel. FIG. 4 shows a flow diagram of this embodiment of a method in accordance with the present invention.

A catheter is inserted into a side-branch vessel (Block 405). The catheter comprises a first inflatable member disposed on a distal portion of the catheter, a first stent disposed on the first inflatable member, a second inflatable member disposed on a proximal portion of the catheter, a third inflatable member disposed on either a distal or a proximal portion of the catheter, and a second stent disposed on the third inflatable member.

The catheter is positioned such that the first stent is at least partially within the side-branch vessel and adjacent the ostium of the vessel (Block 410).

The first inflatable member is inflated to expand the stent within the side-branch vessel (Block 415). The first inflatable member is then deflated (Block 420), and the catheter is advanced to a position such that the second inflatable member is at least partially within the expanded stent and adjacent the ostium of the vessel (Block 425). The first inflatable member is then inflated a second time to anchor the catheter within the side-branch vessel (Block 430).

With the catheter anchored in the vessel by the first inflatable member, the second inflatable member is inflated to conform a portion of the stent to the ostium of the side-branch vessel (Block 435).

The first and second inflatable members are deflated (Block 440), and the catheter is positioned such that the third inflatable member is within the side-branch vessel at a location other than the ostium of the vessel (Block 445). The third inflatable member is inflated to expand the second stent (Block 450). The third inflatable member may become generally cylindrical upon inflation, providing a roughly uniform expansion of the stent. Where the stent includes a therapeutic agent, expanding the stent places the therapeutic agent in contact with the vessel wall. The third inflatable member is then deflated (Block 455), and the catheter is removed from the side-branch vessel (Block 460).

While the embodiments of the invention disclosed herein are presently considered to be preferred, various changes and modifications can be made without departing from the spirit and scope of the invention. The scope of the invention is indicated in the appended claims, and all changes and modifications that come within the meaning and range of equivalents are intended to be embraced therein.

What is claimed is:

1. A system for treating an ostium of a side-branch vessel, comprising:
   a catheter;
   a first inflatable member disposed on a distal portion of the catheter and inflatable to become generally cylindrical;
   a stent disposed on the first inflatable member, the stent having a body portion and an end portion; and
   a conformable second inflatable member disposed on a proximal portion of the catheter and inflatable to become generally spherical, the second inflatable member spaced apart from the first inflatable member such that at least a portion of the first inflatable member is distal to the stent and inflatable to conform a body portion of the stent to a branch vessel when the second inflatable member is in position to be inflated to expand the end portion of the stent into a flared configuration to conform the end portion of the stent to an ostium of a side-branch vessel.

2. The system of claim 1 further comprising at least one radiopaque marker, wherein the radiopaque marker aids in positioning the system.

3. The system of claim 1 wherein the first inflatable member includes a contractile member to aid in returning the first inflatable member to an uninflated configuration upon deflation.

4. The system of claim 1 wherein the body portion and the end portion have different material properties.

5. The system of claim 1 wherein the stent further comprises a therapeutic agent operably disposed on a surface of the stent.

6. A method for treating an ostium of a side-branch vessel, comprising:
   inserting a catheter into a side-branch vessel, the catheter comprising a first inflatable member disposed on a distal portion of the catheter, a first stent disposed on the first inflatable member, and a second inflatable member disposed on a proximal portion of the catheter;
   positioning the catheter such that the first stent is at least partially within the side-branch vessel and adjacent the ostium of the vessel;
   inflating the first inflatable member to expand the first stent;
   deflating the first inflatable member;
   advancing the catheter to a position such that the second inflatable member is at least partially within the expanded stent and adjacent the ostium of the vessel;
   re-inflating the first inflatable member to anchor the catheter within the side-branch vessel;
   inflating the second inflatable member to conform a portion of the stent to the ostium of the side-branch vessel;
   deflating the first and second inflatable members; and
   removing the catheter from the side-branch vessel.

7. The method of claim 6 further comprising using a single guide wire.

8. The method of claim 6 further comprising using a therapeutic agent, the therapeutic agent operably disposed on the stent.

9. The method of claim 6 further comprising using at least one radiopaque marker, the radiopaque marker operably disposed on the catheter.

10. The method of claim 6 wherein inflating the first inflatable member comprises expanding the first inflatable member into a generally cylindrical shape.

11. The method of claim 6 wherein inflating the second inflatable member comprises expanding the second inflatable member into a generally spherical shape.

12. The method of claim 6 wherein inflating the second inflatable member conforms an end portion of the stent to the ostium of the side-branch vessel, the end portion having material properties different from those of a body portion of the stent.

13. The method of claim 6 wherein when delivering the catheter, the catheter further comprises a third inflatable member disposed on one of a distal or a proximal portion of the catheter and a second stent disposed on the third inflatable member.

14. The method of claim 13 further comprising:
prior to removing the catheter from the side-branch vessel, positioning the catheter such that the third inflatable member is within the side-branch vessel at a location other than the ostium of the vessel;
inflating the third inflatable member to expand the second stent; and
deflating the third inflatable member.

15. The method of claim 13 further comprising using a therapeutic agent, the therapeutic agent operably disposed on the second stent.

16. The method of claim 13 wherein inflating the third inflatable member comprises expanding the third inflatable member into a generally cylindrical shape.

* * * * *